United States Patent [19]
Zenzen et al.

[11] Patent Number: 5,336,205
[45] Date of Patent: Aug. 9, 1994

[54] FLOW DIRECTED CATHETER

[75] Inventors: Wendy J. Zenzen, Fremont; Uriel H. Chee, San Carlos, both of Calif.

[73] Assignee: Target Therapeutics, Inc., Fremont, Calif.

[21] Appl. No.: 23,805

[22] Filed: Feb. 25, 1993

[51] Int. Cl.[5] ............................................. A61M 25/00
[52] U.S. Cl. ......................................... 604/280; 604/53
[58] Field of Search ............... 604/280, 282, 158, 164, 604/264, 53; 128/656–658, 673, 692

[56] References Cited

U.S. PATENT DOCUMENTS

| | | | |
|---|---|---|---|
| 3,228,894 | 1/1966 | Jeckel | 604/280 |
| 3,370,587 | 2/1968 | Vizcarra | 604/158 |
| 3,608,555 | 9/1971 | Greyson | 604/280 |
| 3,746,003 | 7/1973 | Blake et al. | |
| 3,749,134 | 7/1973 | Slingluff et al. | 604/280 |
| 3,866,599 | 2/1975 | Johnson | |
| 3,995,623 | 12/1976 | Blake et al. | |
| 4,024,873 | 5/1977 | Antoshkiw et al. | |
| 4,169,464 | 10/1979 | Obrez | 128/657 |
| 4,276,874 | 7/1981 | Wolvek et al. | |
| 4,329,993 | 5/1982 | Lieber et al. | 604/280 |
| 4,385,635 | 5/1983 | Ruiz | 604/280 X |
| 4,596,563 | 6/1986 | Pande | 604/280 X |
| 4,694,838 | 9/1987 | Wijayarthna et al. | 128/658 |
| 4,696,304 | 9/1987 | Chin | 604/280 |
| 4,721,115 | 1/1988 | Owens | |
| 4,739,768 | 4/1988 | Engelson | |
| 4,747,840 | 5/1988 | Ladika et al. | 604/280 |
| 4,758,221 | 7/1988 | Jureidini | |
| 4,762,130 | 8/1988 | Fogarty et al. | |
| 4,883,058 | 11/1989 | Ruiz | 128/658 X |
| 4,884,579 | 12/1989 | Engelson | |
| 4,963,306 | 10/1990 | Weldon | 604/280 X |
| 4,994,069 | 2/1991 | Ritchart et al. | 606/200 X |
| 5,037,404 | 8/1991 | Gold et al. | 604/280 X |
| 5,069,673 | 12/1991 | Shwab | 604/280 |
| 5,171,232 | 12/1992 | Castillo et al. | 128/658 |

FOREIGN PATENT DOCUMENTS

| | | | |
|---|---|---|---|
| 0517075 | 12/1992 | European Pat. Off. | 604/280 |
| 0015356 | 9/1992 | World Int. Prop. O. | 604/280 |

OTHER PUBLICATIONS

Dion, J. E., et al., "Progressive suppleness pursil catheter: A new tool for superselective angiography and embolization" *AJNR* (Sep./Oct. 1989) 10:1068–1070.

Target Therapeutics Product Brochure entitled "Zephyr TM flow-assisted infusion catheter" (1991) Target Therapeutics, 130 Rio Robles, San Jose, Calif. 95134, 4 pages total.

*Primary Examiner*—C. Fred Rosenbaum
*Assistant Examiner*—Frank Wilkens
*Attorney, Agent, or Firm*—Morrison & Foerster

[57] ABSTRACT

An infusion catheter with an elongate tubular body having proximal and distal ends and a lumen extending between the ends through which a diagnostic, therapeutic, or vasoocclusive agent can be delivered is disclosed. The elongate tubular body is formed of a relatively stiff tapered proximal segment, a relatively flexible and strong distal segment, and a transition section that is less flexible than the distal segment but more flexible than the proximal segment. The infusion catheter is directed to the target site by means of the flow of blood to that site.

17 Claims, 2 Drawing Sheets

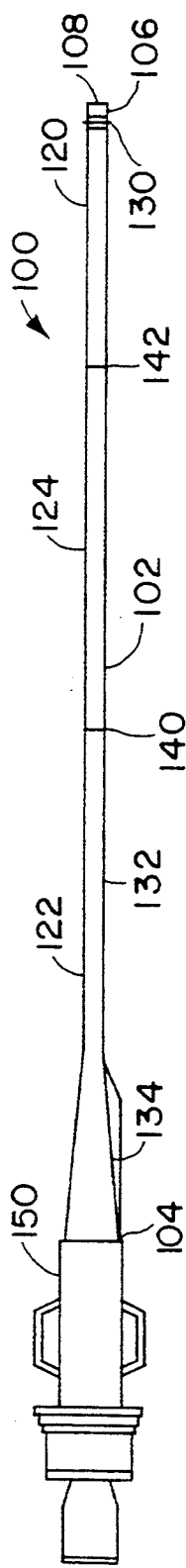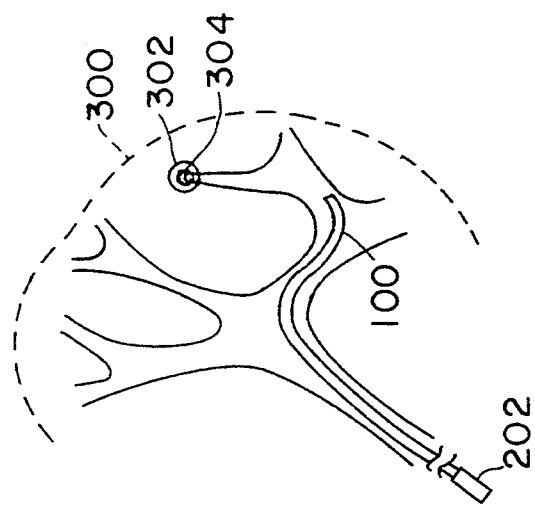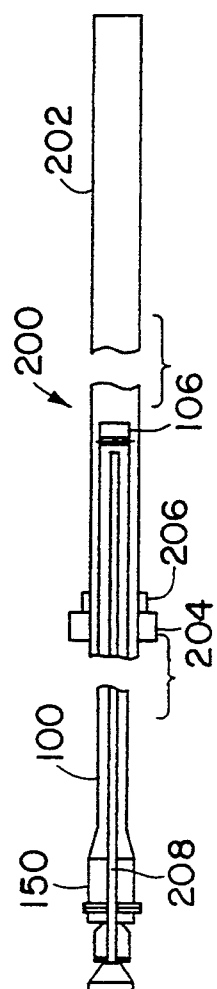

FLOW DIRECTED CATHETER

FIELD OF THE INVENTION

The present invention is in the general field of surgical instruments and relates specifically to infusion catheters that are used in cardiovascular and endovascular procedures to deliver diagnostic, therapeutic or vasoocclusive agents to a target site (the target site being accessible by a tortuous path through the vasculature). The invention also relates to the process of using the infusion catheter.

BACKGROUND

Catheters are being used increasingly as a means for delivering diagnostic or therapeutic agents to internal target sites that can be accessed through the circulatory system. There are a number of general approaches for placing catheters within vessels in the body that are difficult to access. In one such technique, a torqueable guidewire is alternately rotated and advanced to the target site. With the wire in place, the catheter is then advanced along the wire until the distal end of the catheter is positioned at the target site. An example of this technique is described in U.S. Pat. No. 4,884,579. A major drawback to this approach is the time-consuming nature of rotating and advancing the guidewire and catheter through the vasculature.

A second technique for advancing a catheter to a target site is to employ a highly flexible catheter having an inflatable, but pre-punctured balloon at its distal end. In use, the balloon is partially inflated, and carried by blood flow into the target site. During placement, the balloon is continually inflated to replenish fluid leaking from the balloon. This technique, too, has major drawbacks including the fact that the catheter material is so floppy that it cannot be pushed without buckling, and instead must be advanced using injected fluid to inflate the balloon in order to propel the catheter to the target site. Additionally, there is a significant risk of rupture of a vessel by a balloon that has been overinflated.

In order to address some of the above described problems, another approach has involved the use of flexible catheters that can be directed to a target site as a result of the blood flowing to that site. In 1991, Target Therapeutics released a product known as the "ZEPHYR" flow-assisted infusion catheter. The product was designed to be introduced into the vasculature through a guiding catheter and then allowed to be directed by the blood flow to a target site. The catheter comprised segments of different materials, a proximal segment made of nylon, and middle and distal segments made of a block copolymer of polyamide. The product proved to be unsuccessful in achieving its desired function as it was not flexible enough to navigate the tortuous vessel pathway and not strong enough to withstand the required injection pressure.

The present invention is an infusion catheter assembly useful for the delivery of diagnostic, therapeutic or vasoocclusive agents to remote portions of the vascular system, particularly to diagnose or treat arteriovenous malformations (AVMs). The invention also includes a process for placing the infusion catheter at the target site and a process for delivering a diagnostic, therapeutic or vasoocclusive agent to the target site.

SUMMARY OF THE INVENTION

This invention is an infusion catheter for placement within a tortuous, small vessel pathway and a method for delivery of an agent to a target site. The infusion catheter is directed to the target site by means of the flow of blood to that site. The infusion catheter has an elongate tubular body having proximal and distal ends and a lumen extending between the ends through which the diagnostic, therapeutic, or vasoocclusive agent can be delivered.

The elongate tubular body is formed of a relatively stiff tapered proximal segment, a relatively flexible and strong distal segment, and a transition section between the proximal and distal segments that is less flexible than the distal segment but more flexible than the proximal segment. The distal segment has a burst pressure of at least about 195 psi and is made of a material that will show a force of about $1 \times 10^{-4}$ pounds or less when ten centimeters of the material is deflected 10° from horizontal.

A further aspect of the invention is a method for accessing a target site. A guiding catheter is inserted into the vasculature. An infusion catheter is then inserted into the guiding catheter. A stylet may optionally be used to straighten the soft, flexible distal end of the infusion catheter for easy insertion into the guiding catheter. If the stylet is used, it is removed once the infusion catheter is inside the guiding catheter. The infusion catheter is then pushed out of the guiding catheter into the vasculature. The blood flow in the vasculature directs the infusion catheter to the target site.

Yet another aspect of the invention is a method for delivering a diagnostic, therapeutic or vasoocclusive agent to a target site. The infusion catheter is inserted into the vasculature by means of a guiding catheter. The infusion catheter is positioned at the target site as a result of the blood flow to the target site. The diagnostic, therapeutic or vasoocclusive agent is then injected through the catheter lumen and infused into the target site.

BRIEF DESCRIPTION OF THE DRAWINGS

FIG. 1 is a diagram that shows an infusion catheter constructed according to a preferred embodiment of the present invention.

FIG. 2 is a diagram that shows the distal end on one embodiment of the infusion catheter of the present invention wherein the distal end is formed in an "S" shaped configuration.

FIG. 3 is a diagram that shows an infusion catheter, stylet and guiding catheter assembly.

FIG. 4 is an illustration of a portion of a tortuous path in a soft tissue, and the method of guiding the infusion catheter along this path.

DETAILED DESCRIPTION OF THE INVENTION

Figure 5:
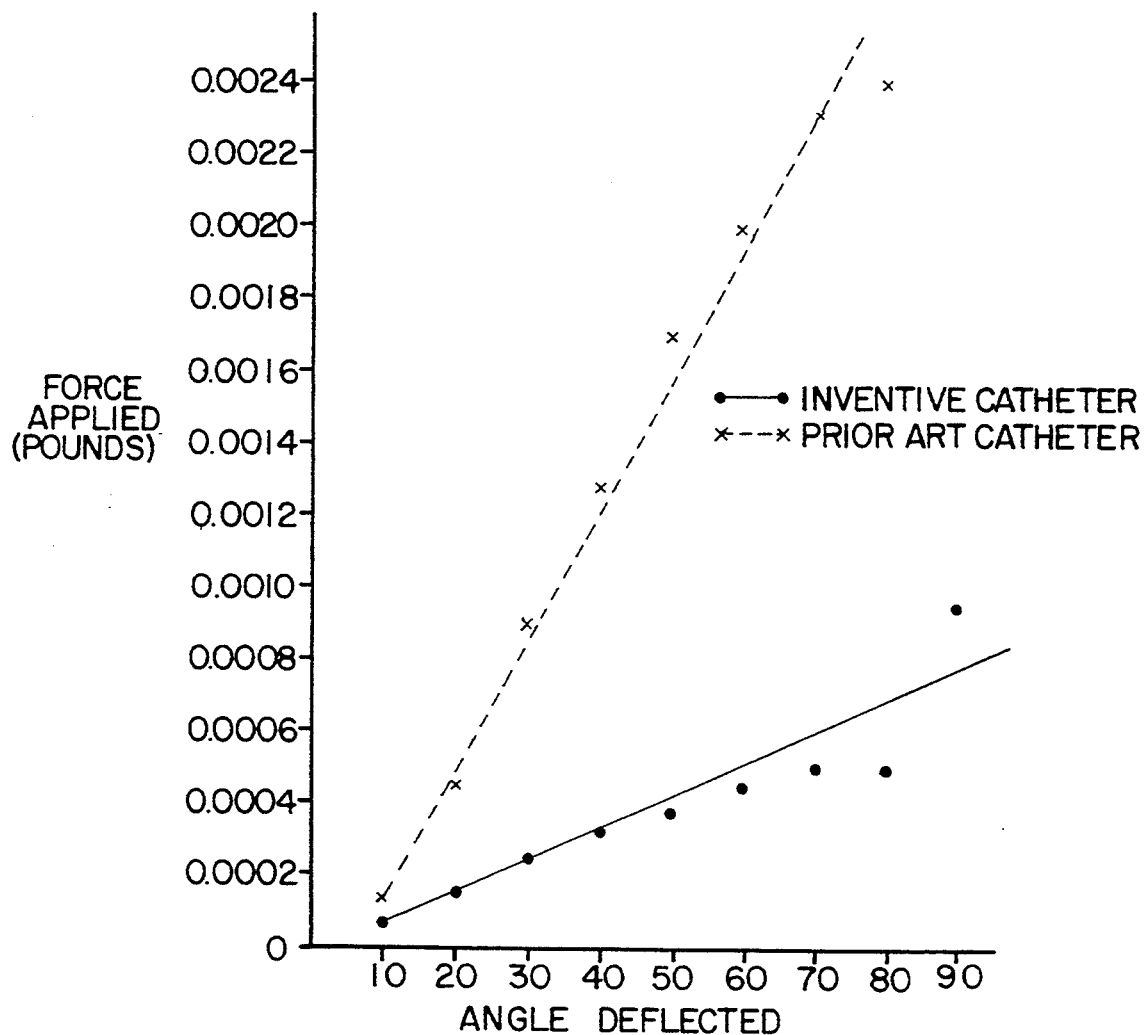
FIG. 5 is a graph showing the pounds of force corresponding to the angle that the distal segment material of the inventive catheter is deflected as compared to the distal segment material of a prior art catheter.

FIG. 1 shows an infusion catheter 100 constructed according to a preferred embodiment of the invention. The catheter 100 has an elongate tubular body 102 with proximal 104 and distal 106 ends and an inner lumen 108 extending between the ends. The elongate tubular body 102 is comprised of three segments; a relatively flexible and strong distal segment 120, a relatively stiff tapered proximal segment 122 and a transition section 124 between the proximal and distal segments that is less flexible than the distal segment 120 but more flexible than the proximal segment 122.

The elongate tubular body 102 has a relatively flexible and strong distal segment 120 such that the catheter can easily navigate a tortuous vessel pathway. By relatively flexible is meant that a force of about $1 \times 10^{-4}$ pounds corresponds to a deflection of the material that is 10° from horizontal, or only about $5 \times 10^{-4}$ pounds of force to deflect the material about 80° from horizontal. By relatively strong is meant that the material has a burst pressure of greater than 195 psi, more preferably the burst pressure is between about 195 and 220 psi.

The flexible distal segment 120 has an open end which allows for the infusion of diagnostic, therapeutic or vasoocclusive agents into the target site. The flexible distal segment 120 is made of a polymer that is springy and biologically compatible such as polyurethane, a block copolymer of polyamide, polyvinyl chloride, or silicone or blends of the above. The flexible distal segment 120 carries one or more radiopaque bands 130 or may be doped with a radiopaque material such as barium sulfate, bismuth trioxide, bismuth subcarbonate, tungsten, tantalum or the like so that the location of the distal region of the catheter within the vessel may be visualized radiographically. The distal segment 120 makes up between about 5 and 25% of the total length of the tubular member and is between about 5 and 40 cm long, preferably between about 10 and 20 cm long. The inner diameter of the distal segment 120 is between about 0.25 and 0.50 mm, more preferably between about 0.25 and 0.35 mm. The outer diameter of the distal segment is between about 0.50 and 0.80 mm, more preferably between about 0.60 and 0.70 mm. The wall thickness of the distal segment 120 is between about 0.1 and 0.3 mm.

The proximal segment 122 of the elongate tubular body 102 is relatively stiff such that it can be easily pushed thus eliminating the need for guidewire support. The proximal segment 122 is made of a polymeric or metallic material that is relatively stiff and biologically compatible such as nylon, polyvinyl chloride, polyethylene terephthalate or other polyester elastomers or a braided shaft (a polymer outer core with a metallic mesh inner core). The proximal segment 122 comprises a tapered proximal section 134 for attachment to the proximal end fitting 150 and a distal section 132. The proximal section 134 of proximal segment 122 makes up between about 60% and 80% of the total length of the tubular member 102 and is between about 90 and 130 cm long, preferably between about 100 and 120 cm long. The largest inner diameter of the proximal section 134 (at the proximal end 104 of the tubular member 102) is between about 0.40 and 0.60 mm, more preferably between about 0.45 and 0.55 mm. The outer diameter of the proximal section 134 at the proximal end 104 of the tubular member 102 is between about 0.8 and 1.2 mm. The wall thickness of the proximal section 134 of proximal segment 122 is between about 0.1 and 0.4 mm, more preferably between about 0.2 and 0.3 mm.

The distal section 132 of proximal segment 122 makes up between 10 and 20% of the total length of the tubular body 102 and is between about 20 and 40 cm long, preferably between about 20 and 30 cm long. The inner diameter of the distal section 132 of proximal segment 122 is between about 0.20 and 0.50 mm, more preferably between about 0.25 and 0.35 mm. The outer diameter of the distal section 132 of proximal segment 122 is between about 0.60 and 0.90 mm, more preferably between about 0.60 and 0.70 mm. The wall thickness of the distal section 134 of proximal segment 122 is between about 0.1 and 0.3 mm.

The transition section 124 of the elongate tubular body 102 is less stiff than the proximal segment 122 but more stiff than the distal segment 120. A suitable material that is biologically compatible is a polymer such as polyurethane, a block copolymer of polyamide, polyvinyl chloride or silicone with greater durometer (i.e. that is stiffer) than the flexible distal segment 120. The transition section 124 may be radiopaque and thus observable in the event that the catheter becomes lodged in a particular portion of the vasculature or buckles, and as such the polymeric material is doped with a radiopaque material such as barium sulfate, bismuth subcarbonate, bismuth trioxide, tungsten, tantalum or the like. The transition section 124 makes up between about 10 and 20% of the total length of the tubular member 102 and is between about 20 and 40 cm long, preferably between about 25 and 35 cm long. The transition section 124 may be of constant diameter or may be tapered. The inner diameter of the transition section 124 is between about 0.20 and 0.50 mm, more preferably between about 0.20 and 0.35 mm. The outer diameter of the transition section 124 is between about 0.50 and 0.90 mm, more preferably between about 0.60 and 0.70 mm. The wall thickness of the transition section 124 is between about 0.1 and 0.3 mm.

The proximal segment 122, transition section 124 and distal segment 120 are joined at junctions 140 and 142, respectively. The junctions are formed by flaring, overlapping and heat fusing the materials of the proximal segment 122 and transition section 124 and the transition section 124 and distal segment 120. The distal segment 120, transition section 124 and distal section 132 of proximal segment 122 may all have approximately the same outside diameter or the transition section 124 and the distal section 132 of the proximal segment 122 may be tapered.

A standard proximal end fitting 150 is attached to the proximal section 134 of the proximal segment 122 by heat fusion with reinforcing tubing.

FIG. 2 shows one embodiment of the distal segment 120 of the catheter wherein the tip 160 of the catheter is shaped with steam such that the distal end 106 points to the wall of the vessel rather than straight into the path of blood flow for ease of manipulation through the tortuous vessel pathway. The particular embodiment shown is an "S" shape, but the tip may be any shape that allows for access to the particular vasculature being treated. In this way, if the catheter becomes lodged against the vessel wall, the infusion of liquid through the catheter propels the distal end 106 of the catheter away from the vessel wall. As the stiff proximal segment 122 is pushed, the distal segment 120 will be carried by the blood flood to the target site.

The catheter described above is useful in delivering diagnostic, therapeutic, or vasoocclusive agents to deep tissue.

FIG. 3 shows a catheter assembly 200 for placing the infusion catheter 100 at the target site. An appropriate guiding catheter 202 is inserted into the vasculature using standard placement techniques. A rotating hemostatic valve 204 is connected to the guiding catheter luer adapter 206. The guiding catheter 202 is continuously flushed with saline. The thumb-screw of the valve 204 is opened and the infusion catheter 100 is inserted through the rotating hemostatic valve 204. Optionally, as shown in FIG. 3, a teflon-coated stainless steel styler 208 is first inserted into the infusion catheter 100 in order to prevent kinking of the infusion catheter 100 within the valve 204. The distal end 106 of the infusion catheter 100 is advanced proximal to the tip of the guiding catheter 202. The stylet 208 is then removed from the infusion catheter 100. Once the stylet 208 is removed, the infusion catheter 100 is pushed out of the guiding catheter 202. The infusion catheter 100 is gently guided by the flow of blood in the vasculature to the target site. Optionally, gentle pushing and pulling and injection of saline or contrast medium through the catheter lumen 108 may aid in the placement of the catheter at the target site.

FIG. 4 shows the method of inserting the infusion catheter into a tissue region which is reached by a tortuous path. The figure shows a region of soft tissue 300, such as in the region of the brain, containing a target site 302. Initially the guiding catheter, indicated at 202 is fed from a vascular access region. The infusion catheter 100 is inserted into the guiding catheter 202 and then pushed out of the end of the guiding catheter. Blood flow in the vessel then directs the infusion catheter 100 to the target site 302.

Once the infusion catheter is placed at the target site, a syringe may be connected to the proximal end fitting 150 and the diagnostic, therapeutic or vasoocclusive agent may be infused through the catheter lumen 108 and into the target site. The injected agent may include radiopaque agents for viewing blood vessel anatomy and blood flow characteristics in the target region, vasoocclusive agents which can be used to produce small-artery vasoocclusion in the tissue region supplied by the target vessel, and pharmacological agents, such as anti-tumor drugs or sclerosing agents such as alcohols, which are effective against identified disease states at the target site. Vasoocclusive agents useful in the treatment of arteriovenous malformations include polymers that are activated in the presence of polar solvents such as water and include materials such as n-butylcyanoacrylate. Other types of vasoocclusive agents useful in the treatment of arteriovenous malformations include polymer solutions that coagulate by diffusion of the solvent when in contact with blood. Polyvinyl acetate dissolved in dimethylsulfoxide is one such agent. Alternatively, vasoocclusive coils (304) may be injected into the infusion catheter and delivered to a target site to occlude the blood flow at that site.

The following Examples are intended to illustrate the invention but not to limit it in any manner.

EXAMPLES

Example 1—Comparison of Burst Pressures

Prior art catheters, in particular the "ZEPHYR" catheter first marketed in 1991 were tested for burst pressure as were the inventive catheters. Pressure was applied by injecting liquid with pressures in the range of 0 to burst in 25–30 psi increments into the proximal end fitting of the catheter. The prior art catheter burst at the distal end when approximately 141 psi of pressure was applied. This value was a mean value for the catheters tested and therefore, statistically, 99.73% (3 sigma) of the values for burst pressure for the prior art catheters lie between about 97 and 185 psi. The catheters of the present invention burst at the distal end when a mean value of 207 psi of pressure was applied. 99.73% (3 sigma) of the values for burst pressure for the inventive catheters, therefore, lie between about 195 and 220 psi. The inventive catheters, therefore proved to be stronger than the prior art catheters.

Example 2—Testing of Distal End Flexibility

The flexibilities of the distal ends of the prior art "ZEPHYR" catheter and the inventive catheters were compared using a Tinius Olsen bending stiffness tester. The results are graphically described in FIG. 5.

10 centimeter portions of the distal segments of each catheter were placed on the steel plate of the Olsen stiffness tester. The material was deflected to different positions and the corresponding pounds of force recorded. When the inventive catheter was deflected 10°, the stiffness tester showed a force of $7 \times 10^{-5}$ pounds, when it was deflected 50° the force was $3.8 \times 10^{-4}$ pounds, and when the deflection was 80°, the force was $4.9 \times 10^{-4}$ pounds. The prior art catheter was deflected 10° and the stiffness tester showed a force of $7.5 \times 10^{-3}$ pounds, when it was deflected 50° the force was $8.5 \times 10^{-2}$ pounds, and when the deflection was 80°, the force was $1.23 \times 10^{-1}$ pounds. The inventive catheter, therefore, proved to be much more flexible than the prior art catheter. Upon calculation of the slope of the lines shown in FIG. 5, for the inventive catheter, a 1° deflection corresponds to $10^{-5}$ pounds of force, and for a prior art catheter, a 0.3° deflection corresponds to $10^{-5}$ pounds of force.

While preferred embodiments of the invention have been described herein, it will be recognized that a variety of changes and modifications can be made without departing from the invention.

We claim:

1. A catheter that can be guided by the blood flow within a vessel, said catheter comprising an elongate tubular member having proximal and distal ends and an inner lumen extending between these ends, said member comprising:
   (a) a tapered proximal segment that is between about 110 and 160 cm long and has a wall thickness of between about 0.1 and 0.4 mm, an outer diameter of between about 0.6 and 1.2 mm, and an inner diameter of between about 0.2 and 0.6 mm;
   (b) a distal segment that is between about 5 and 40 cm long and has a wall thickness of between about 0.1 and 0.3 mm, an outer diameter of between about 0.5 and 0.8 mm, and an inner diameter of between about 0.25 and 0.5 mm; and
   (c) a transition section between said proximal and said distal segments that is between about 20 and 40 cm long and has a wall thickness of between about 0.1 and 0.3 mm, an outer diameter of between about 0.5 and 0.9 mm, and an inner diameter of between about 0.2 and 0.5 mm;
   wherein said distal segment has a burst pressure of at least about 195 psi and is made of a material which will show a force of about $10^{-4}$ pounds or less when ten centimeters of the material is deflected 10° from horizontal.

2. The catheter of claim 1 wherein the burst pressure of the distal segment is between about 195 and 220 psi.

3. The catheter of claim 1 wherein the distal section is made of a material that further will show an additional force of about $10^{-5}$ pounds or less for each 1° of deflection of the material from horizontal.

4. The catheter of claim 1 wherein the proximal segment is made of a polymeric material selected from the group consisting of nylon, polyvinyl chloride, polyethylene terephthalate or other polyester elastomer or of a polymer outer core with a metallic mesh inner core.

5. The catheter of claim 1 wherein the distal segment is made of a polymeric material selected from the group consisting of polyurethane, a block copolymer of polyamide, polyvinyl chloride, silicone and blends thereof.

6. The catheter of claim 5 wherein the polymeric material of the distal segment is doped with a metallic material selected from the group consisting of barium sulfate, bismuth trioxide, bismuth subcarbonate, tungsten and tantalum.

7. The catheter of claim 1 wherein the transition section is made of a polymeric material selected from the group consisting of polyurethane, a block copolymer of polyamide, polyvinyl chloride, and silicone.

8. The catheter of claim 7 wherein the polymeric material of the transition section is doped with a metallic material selected from the group consisting of barium sulfate, bismuth trioxide, bismuth subcarbonate, tungsten and tantalum.

9. The catheter of claim 1 wherein the distal segment is in an S-shaped configuration.

10. A method for accessing a target site, said method comprising:
  (a) inserting a guiding catheter into the vasculature;
  (b) inserting the infusion catheter of claim 1 into the guiding catheter; and
  (c) pushing the infusion catheter out of the guiding catheter into the vasculature such that the blood flow in the vessel directs the infusion catheter to the target site.

11. The method of claim 10 which further comprises inserting a stylet into the infusion catheter in order to insert the catheter into the guiding catheter and further removing the stylet prior to pushing the infusion catheter out of the guiding catheter and into the vasculature.

12. The method of claim 11 wherein the stylet is a teflon-coated stainless steel stylet.

13. A method for delivering a diagnostic, therapeutic or vasoocclusive agent to a target site within the vasculature, said method comprising:
  (a) inserting a guiding catheter into the vasculature;
  (b) inserting the infusion catheter of claim 1 into the guiding catheter;
  (c) pushing the infusion catheter out of the guiding catheter into the vasculature such that the blood flow in the vasculature directs the infusion catheter to the target site; and
  (d) injecting the diagnostic, therapeutic or vasoocclusive agent through the catheter lumen and into the target site.

14. The method of claim 13 which further comprises inserting a stylet into the infusion catheter in order to insert the catheter into the guiding catheter and further removing the stylet prior to pushing the infusion catheter out of the guiding catheter and into the vasculature.

15. The method of claim 13 wherein the vasoocclusive agent is n-butylcyanoacrylate and the target site is an arteriovenous malformation.

16. The method of claim 13 wherein the vasoocclusive agent is polyvinylacetate dissolved in dimethylsulfoxide and the target site is an arteriovenous malformation.

17. The method of claim 13 wherein the vasoocclusive agent is a vasoocclusive coil.

* * * * *